United States Patent [19]

Hutchison

[11] Patent Number: 5,071,858
[45] Date of Patent: Dec. 10, 1991

[54] ANTIPSYCHOTIC BENZOTHIOPYRANYLAMINES

[75] Inventor: Alan J. Hutchison, Verona, N.J.

[73] Assignee: Ciba-Geigy Corporation, Ardsley, N.Y.

[21] Appl. No.: 597,299

[22] Filed: Oct. 12, 1990

Related U.S. Application Data

[63] Continuation of Ser. No. 326,949, Mar. 22, 1989, abandoned.

[51] Int. Cl.$^5$ .................. A61K 31/445; C07D 211/40
[52] U.S. Cl. .................................. 514/324; 514/212;
514/422; 514/443; 540/596; 546/202; 548/525;
549/23
[58] Field of Search ............... 514/212, 324, 422, 443;
540/596; 546/202; 548/525; 549/23

[56] References Cited

U.S. PATENT DOCUMENTS

| 3,714,190 | 1/1973 | Boissier et al. | 260/327 |
| 3,944,551 | 3/1976 | Regnier et al. | 544/369 |
| 4,104,396 | 8/1978 | Huebner | 514/321 |
| 4,468,404 | 8/1984 | Rane et al. | 544/366 X |
| 4,497,820 | 2/1985 | Merlini et al. | 514/432 |
| 4,745,114 | 5/1988 | Elliott et al. | 514/233.5 |
| 4,801,605 | 1/1989 | Hutchison | 514/432 |
| 4,847,254 | 7/1989 | Boegesae et al. | 514/256 |

FOREIGN PATENT DOCUMENTS

| 8662317 | 3/1987 | Australia . |
| 0252005 | 1/1988 | European Pat. Off. . |
| 0325964 | 8/1989 | European Pat. Off. . |

OTHER PUBLICATIONS

Chem. Abstract vol. 88 (1978) 376172.
Tetrahedron Letters 1976 4355-4358.
Derwant Abstract 84-192864/31 af J.P. 5-9110-690 (1984).
Hori et al., "Formation of Novel Heterocycles . . . " Heterocycles vol. 23 No. 6; pp. 1381-1384 (1985).
Hattersley et al., "Some Alkylation and Grignard Reactions . . . " J. Chem. Soc. c. 1969, pp. 217-222.
Nakanishi et al., Chem. Abstr. vol. 74:13006j (1971).
Hansen et al., Chem. Abstr. vol. 74:13005h (1971).
Chu et al., Chem. Abstr. vol. 52:11044a f (1957).
Derwent Abstract of Japan 1,052,718; 2/29/89.
Chu et al., Chem. Abstracts vol. 53:7160i–7162a (1959).
Sen. et al., Chem. Abstr. vol. 53:15069a (1959).
Gupta et al., Indian J. Chem. vol. 21B pp. 344-347 (1982).
Sen. et al., J. Indian Chem. Soc. vol. 43, pp. 521-525 (1987).
Mouysset et al., Eur. J. Med. Chem. vol. 22 pp. 539-544 (1987).
Duncan et al., J. Med. Chem. vol. 13 pp. 1-6 (1970).

Primary Examiner—Mary C. Lee
Assistant Examiner—Jacqueline Haley
Attorney, Agent, or Firm—Norbert Gruenfeld

[57] ABSTRACT

Disclosed are 3,4-dihydro-2H-1-benzothiopyran-3-yl-methyl- and ethylamines useful as antipsychotics, processes for the preparation of said compounds, pharmaceutical compositions containing same, and a method of treating psychotic disorders by administering said compounds.

15 Claims, No Drawings

ANTIPSYCHOTIC BENZOTHIOPYRANYLAMINES

This application is a continuation of application Ser. No. 326,949, filed Mar. 22, 1989, abandoned.

The present invention is concerned with 3,4-dihydro-2H-1-benzothiopyran-3-ylmethyl- and ethylamines useful as antipsychotics, processes for the preparation of said compounds, pharmaceutical compositions containing same, and a method of treating psychotic disorders by administering said compounds.

In particular, the invention is concerned with benzothiopyranylmethyl- and ethylamines of the formula

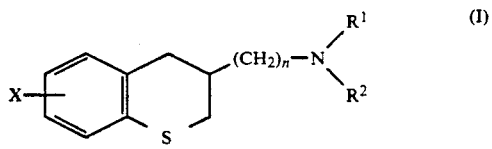

wherein n is one or two, X represents hydrogen, halogen, lower alkyl, hydroxy or lower alkoxy, $R^1$ is lower alkyl, $R^2$ is lower alkyl substituted by A, or $R^1$ and $R^2$ together represent alkylene of 4 to 6 carbon atoms substituted by A, and A is hydrogen, hydroxymethyl, hydroxy-arylmethyl, hydroxy-diarylmethyl, lower alkoxymethyl, aryl-lower alkoxymethyl, lower alkanoyloxymethyl, aryl-lower alkanoyloxymethyl, aroyloxymethyl, lower alkanoyl, aryl-lower alkanoyl, aroyl, lower alkoxycarbonyl, or aryl-lower alkoxycarbonyl, and salts thereof.

The general definitions used herein have the following meaning within the scope of the present invention.

The term "lower" referred to above and hereinafter in connection with organic radicals or compounds, respectively, defines, such with up to and including 7, preferably up to and including 4, and advantageously one or two carbon atoms.

A lower alkyl group contains 1 to 7 carbon atoms, preferably 1 to 4 carbon atoms, is advantageously straight chain and represents for example methyl, ethyl, propyl or butyl.

Alkylene of 4 to 6 carbon atoms (for $R^1$ and $R^2$ combined) represents preferably straight chain butylene, pentylene or hexylene to form together with the nitrogen atom pyrrolidino, piperidino or perhydroazepino, respectively.

A lower alkoxy group preferably contains 1–4 carbon atoms and represents, for example, ethoxy, propoxy, isopropoxy or advantageously methoxy.

A lower alkanoyl group contains 1 to 7 carbon atoms, preferably 1 to 4 carbon atoms, and is, for example, formyl, acetyl, propionyl, n-butyryl, isobutyryl, or n-hexanoyl, preferably acetyl or propionyl.

Aryl represents a carbocyclic or heterocyclic aromatic radical, for example unsubstituted or substituted phenyl, naphthyl, furyl, thienyl, pyrrolyl, thiazolyl or pyridyl. Aryl is preferably phenyl or phenyl substituted by one, two or three, preferably one, of lower alkyl, for example methyl, phenyl, hydroxy, lower alkoxy, for example methoxy, halogen, for example chloro or fluoro, or trifluoromethyl. Such substituted phenyl is, for example, o-, m- or p-tolyl, 3,4-xylyl, 2,6-xylyl, p-biphenylyl, p-hydroxyphenyl, o- or p-methoxyphenyl, 3,4-dimethoxyphenyl, o-, m- or p-chlorophenyl, 2,4- or 3,4-dichlorophenyl, 3-chloro-4-methylphenyl, m- or p-fluorophenyl, 2,4-difluorophenyl, 3-chloro-4-fluorophenyl, 4-chloro-3-fluorophenyl, m- or p-trifluoromethylphenyl, or 4-chloro-3trifluoromethylphenyl.

Aroyl is one of the mentioned carbocyclic or heterocyclic aromatic radicals connected to carbonyl, for example naphthoyl, furoyl, thenoyl, pyrrolylcarbonyl or pyridylcarbonyl, or in particular benzoyl or substituted benzoyl, wherein the substituents have the meanings mentioned above, for example o-, m- or p-toluoyl, p-phenylbenzoyl, p-hydroxybenzoyl, p-anisoyl, p-chloro- or pfluorobenzoyl or m-trifluoromethylbenzoyl.

Aryl-lower alkyl is preferably benzyl or 2-phenylethyl, optionally substituted on the phenyl ring as defined under aryl.

Aryl-lower alkanoyl is preferably phenylacetyl, optionally substituted on the phenyl ring as defined under aryl.

Halogen preferably represents chloro or fluoro but may also be bromo or iodo.

The 3,4-dihydro-2H-1-benzothiopyran-3-ylmethyl- and ethylamines of this invention may also be called 3,4-dihydro-2H-benzo[b]thiin-3-ylmethyl- and ethylamines according to generally accepted nomenclature rules.

Depending on the nature of the substituents and the resulting number of asymmetric carbon atoms, the compounds of the invention exist in the form of a number of racemates and optical antipodes thereof. Thus compounds of the invention can exist in the form of stereoisomers, e.g. diastereoisomers, racemates, pure enantiomers or mixtures thereof, all of which are within the scope of the invention.

Compounds of formula I are basic in nature and readily form acid addition salts. Said acid addition salts preferably are pharmaceutically acceptable, non-toxic salts, for example salts with strong mineral acids, for example hydrohalic, e.g. hydrochloric or hydrobromic acid, sulfuric, phosphoric, nitric or perchloric acid; with aliphatic or aromatic carboxylic acids, e.g. formic, acetic, propionic, succinic, glycolic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicyclic, 4-aminosalicyclic, pamoic, or nicotinic acid; or with sulfonic acids, e.g. methanesulfonic, ethanesulfonic, hydroxyethanesulfonic, benzenesulfonic, p-toluenesulfonic, naphthalenesulfonic, sulfanilic or cyclohexylsulfamic acid.

For isolation or purification it is also possible to use pharmaceutically unacceptable salts. However, only the pharmaceutically acceptable non-toxic salts are used therapeutically and these are therefore preferred.

The compounds of the invention are useful in mammals, primarily as serotonin-2 receptor antagonists and as therapeutic agents for the treatment of disorders and conditions which are responsive to the action of a serotonin-2 receptor antagonist, including disorders of the central nervous system, the cardiovascular system and the gastrointestinal system.

The above-cited properties are demonstrable in in vitro and in vivo tests, using advantageously mammals, e.g. rats, dogs, monkeys or isolated organs, tissues and preparations thereof. Said compounds can be applied in vitro in the form of solutions, e.g. preferably aqueous solutions, and in vivo either enterally or parenterally, advantageously orally or intravenously, e.g. within gelatin capsules, as starch suspensions or in aqueous solutions. The dosage in vitro may range between about $10^{-6}$ molar and $10^{-9}$ molar concentrations. The dosage in vivo may range between about 0.10 and 30 mg/kg/day, preferably between about 0.50 and 20 mg/kg/day, advantageously between about 1.0 and 10 mg/kg/day.

The compounds described above are active e.g. in the following test system indicative of serotonin-2 receptor antagonism: The serotonin-2 receptor (also named 5-hydroxytryptamine-2 or 5HT-2 receptor) binding properties are determined in vitro by measuring the ability of said compounds to inhibit the specific binding of $^3$H-ketanserin in membrane preparations of frontal/parietal cortex from male Sprague-Dawley rats essentially as described by Battaglia et al. in Life Sciences 33, 2011 (1983). $IC_{50}$ values, representing the concentration of compound required to displace 50% of $^3$H-ketanserin, are determined by log-logit analysis of the specific binding data. Illustrative of the invention, the compound of example 1 is effective in the serotonin-2 receptor binding assay having an $EC_{50}$ value of about 5 nM.

Compounds of the invention also display moderate dopamine and alpha receptor antagonism as shown in striatal $^3$H-spiperone binding displacement and forebrain $^3$H-prazosin binding displacement.

The serotonin-2 antagonism or blockade is demonstrated in vivo by measuring the inhibition of the head twitch induced by 5-hydroxytryptophan (the metabolic precursor of serotonin) in the rat. The head twitch test for assessing central nervous system serotonin-2 receptor antagonism in the rat is described in Neuropharmacology 16, 663 (1977) and in J. Pharmacol. Esp. Ther. 228, 133 (1984). The test is carried out as follows: Male Wistar rats (120-180 g) are fasted for 18 hours prior to testing but allowed water ad libitum. All animals are pretreated with the peripheral decarboxylase inhibitor alpha-methyl-DOPA hydrazine (carbidopa, 25 mg/kg i.p., 4.0 ml/kg) followed 30 minutes later by 5-hydroxy-tryptophane (5-HTP, 100 mg/kg s.c., 4.0 ml/kg). Ninety minutes after receiving 5-HTP, the rats are placed individually in plexiglass observation cages and the frequency of head twitches for each animal is counted over a 10 minute observation period. The test compound or vehicle is administered at either 0.5 hour at 1.0 ml/kg i.p. or at 1, 2 or 4 hours at 10 ml/kg p.o. prior to the observation period. $ED_{50}$ values are determined by probit analysis. Illustrative of the invention, the compound of example 1 is effective in the head twitch test at a dose of about 0.8 mg/kg i.p.

Further biological effects of the compounds of the invention attributable to the serotonin-2 receptor blocking properties of the, compounds, e.g. effects on the central nervous and cardiovascular systems, can be determined using animal tests well-known in the art. For example, effects indicative of anxiolytic properties may be seen in the standard Cook-Davidson conflict model in the rat; an increase in punished operant performance is indicative of an anti-anxiety effect. Antihypertensive properties can be demonstrated in the spontaneous hypertensive rat and in anesthetized, normotensive dogs. Antithrombotic effects can be demonstrated by the inhibition of serotonin-induced platelet aggregation.

Antipsychotic (neuroleptic) properties are demonstrated in the standard Sidman avoidance model. The test is carried out as follows: Adult male squirrel monkeys (*Samiri sciureus*, 700-1200 g) are trained to press a lever to delay by 20 sec. the delivery of a brief electrical footshock. If the animal fails to respond within a 20 sec. interval, brief (0.5 sec.) shocks (5 mA) are delivered every 20 sec. until the animal again presses the lever. The total number of avoidance responses and avoidance failures (shocks received) are recorded during the test session, which lasts 4 hours. The monkeys are tested two days per week, the first day serving as a baseline control. The test compound is administered orally in a cornstarch vehicle 10 min. prior to the start of the test session. Illustrative of the invention, the compound of example 1 shows avoidance blockade at 0.3 mg/kg p.o. The compounds of the invention block Sidman avoidance responding at lower doses than required to induce the acute dyskinetic syndrome. An approximate dose ratio of three between avoidance blockade and induction of dyskinesias is found for the compound of example 1.

The aforesaid advantageous properties render the compounds of the invention useful in mammals, especially as serotonin-2 receptor antagonists, for the treatment of central nervous system disorders such as anxiety, psychotic disorders, depression and mania, but also for the treatment of gastro-intestinal disorders such as ulcers, and of cardiovascular disorders such as hypertension and thrombosis.

The compounds of the present application, which inhibit serotonergic function at central serotonin-2 receptors, are contemplated to be especially useful as anxiolytic and antipsychotic agents for the treatment of anxiety and psychotic disorders, e.g. schizophrenia, particularly as such cause little or no sedation or impairment of performance at effective doses, and have a low propensity to cause tardive dyskinesia and acute extrapyramidal disorders.

Particularly useful are compounds of formula I, wherein n is one; X represents hydrogen, halogen, for example chlorine, fluorine or bromine, lower alkyl, for example methyl, or lower alkoxy, for example methoxy; $R^1$ is lower alkyl, for example methyl or ethyl; $R^2$ is lower alkyl, for example methyl or ethyl, or aroyl-lower alkyl, for example benzoyl- or fluorobenzoyl-ethyl, -propyl or -butyl; or $R^1$ and $R^2$ together represent straight chain alkylene of 4 to 6 carbon atoms substituted by A, for example butylene or pentylene substituted by A in beta- or gamma-position, and A is hydrogen, hydroxymethyl, hydroxy-arylmethyl, for example alpha-hydroxybenzyl or alpha-hydroxyfluorobenzyl, hydroxy-diarylmethyl, for example alpha-hydroxydiphenyl-methyl or alpha-hydroxydi(fluorophenyl)-methyl, lower alkoxymethyl, for example methoxymethyl or ethoxymethyl, aryl-lower alkoxymethyl, for example benzyloxymethyl, fluorobenzyloxymethyl or 2-phenyl- or fluorophenylethoxymethyl, lower alkanoyloxymethyl, for example acetoxymethyl or propionoxymethyl, aryl-lower alkanoyloxymethyl, for example phenylacetoxymethyl or fluorophenylacetoxymethyl, aroyloxymethyl, for example benzoyloxymethyl, chlorobenzoyloxymethyl or fluorobenzoyloxymethyl, lower alkanoyl, for example acetyl, propionyl or isobutyryl, aryl-lower alkanoyl, for example phenylacetyl, fluorophenylacetyl or beta-fluorophenylpropionyl, aroyl, for example benzoyl, chlorobenzoyl or fluorobenzoyl, lower alkoxycarbonyl, for example methoxy-, ethoxy-, isopropoxy- or n-butoxycarbonyl, or aryl-lower alkoxycarbonyl, for example benzyloxycarbonyl, and acid addition salts thereof.

Preferred are compounds of formula I, wherein n is one or two, X represents hydrogen, halogen, lower alkyl or lower alkoxy, $R^1$ is lower alkyl and $R^2$ is lower alkyl or aroyl-lower alkyl, or $R^1$ and $R^2$ together are straight chain butylene or pentylene; and pharmaceutically acceptable acid addition salts thereof; or compounds of formula

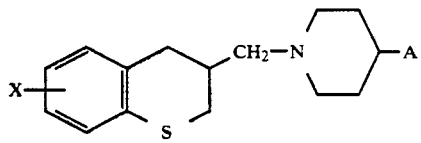

wherein X represents hydrogen, halogen, lower alkyl or lower alkoxy, and A is hydrogen, hydroxymethyl, alpha-hydroxybenzyl, alpha-hydroxydiphenylmethyl, lower alkoxymethyl, phenyl-lower alkoxymethyl, lower alkanoyloxymethyl, phenyl-lower alkanoyloxymethyl, benzoylmethyl, lower alkanoyl, phenyl-lower alkanoyl, benzoyl, lower alkoxycarbonyl or phenyl-lower alkoxycarbonyl, and wherein the phenyl group in phenyl, benzyl and benzoyl is unsubstituted or substituted by halogen, for example chloro or fluoro, in o-, m- or p-position, preferably in p-position, and pharmaceutically acceptable acid addition salts thereof.

Particularly preferred are compounds of formula I wherein n is one, X represents hydrogen, halogen, lower alkyl or lower alkoxy, $R^1$ is lower alkyl, $R^2$ is lower alkyl or aroyl-lower alkyl, or $R^1$ and $R^2$ together represent straight chain butylene or pentylene, especially such compounds wherein $R^1$ is lower alkyl and $R^2$ is aroyl-lower alkyl, for example p-fluorobenzoyl-lower alkyl, and such compounds wherein $R^1$ and $R^2$ together represent straight chain butylene; and pharmaceutically acceptable acid addition salts thereof. Highly preferred are compounds of formula I wherein n is one, X represents fluoro and is located in the 6-position, and $R^1$ is lower alkyl and $R^2$ is p-fluorobenzoyl-lower alkyl, or $R^1$ and $R^2$ together represent straight chain butylene; and pharmaceutically acceptable acid addition salts thereof.

Other particularly preferred compounds are those of formula IA, wherein X represents hydrogen, halogen, lower alkyl or lower alkoxy, and A is hydrogen, hydroxymethyl, alpha-hydroxydi(p-fluorophenyl)methyl, lower alkoxymethyl, p-fluoroben-zyloxymethyl, p-fluorobenzoyloxymethyl, p-fluorobenzoyl, or lower alkoxycarbonyl; and pharmaceutically acceptable acid addition salts thereof.

Highly preferred are compounds of formula IA wherein X represents fluoro and is located in 6-position, and A represents alpha-hydroxydi(p-fluorophenyl)-methyl, p-fluorobenzyloxymethyl, p-fluorobenzoyloxymethyl, or p-fluorobenzoyl; and pharmaceutically acceptable acid addition salts thereof.

Most preferred are the compounds described in the examples, in particular the compound of formula IA wherein X represents fluoro and is located in 6-position and A represents p-fluorobenzoyl; and pharmaceutically acceptable acid addition salts thereof.

The present invention relates also to processes for the manufacture of compounds of formula I and salts thereof. These can be prepared according to methods known per se to those skilled in the art, for example by:

(a) reacting a compound of the formula

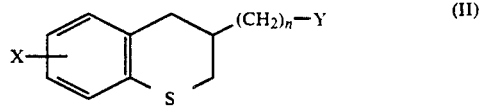

with an amine $R^1R^2NH$, wherein n, X, $R^1$ and $R^2$ have the meaning as previously defined and Y is a leaving group, or (b) reacting a compound of the formula

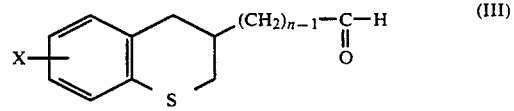

with an amine $R^1R^2NH$ under reducing conditions, wherein n, X, $R^1$ and $R^2$ have the meaning as previously defined, or (c) reacting a compound of the formula

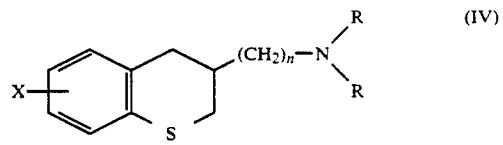

with an alkylating agent $R^0Y$, wherein n and X have the meaning as previously defined, Y is a leaving group, R is a residue $R^1$ or $R^2$ and $R^0$ represents the other residue $R^2$ or $R^1$, respectively, or R is hydrogen and $R^0Y$ represents a bifunctional alkylating agent $Y-R^1-R^2-Y$ wherein $R^1$ and $R^2$ together represent alkylene of 4 to 6 carbon atoms substituted by A as previously defined, or (d) reducing a compound of the formula

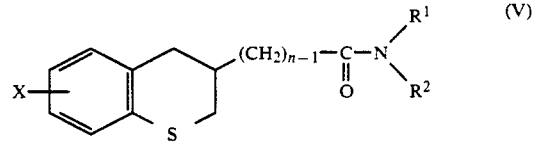

wherein n, X, $R^1$ and $R^2$ have the meaning as previously defined, or (e) reducing a compound of the formula

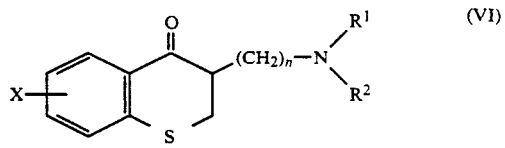

wherein n, X, $R^1$ and $R^2$ have the meaning as previously defined, and, if desired, converting a resulting compound of formula I into another compound of formula I according to the definition, and, if desired, converting a resulting compound of formula I into a salt thereof or converting a resulting salt of a compound of formula I into the free compound or into another salt thereof, and, if required, separating a mixture of isomers or racemates obtained into the single isomers or racemates, and, if desired, resolving a racemate obtained into the optical antipodes.

In process (a) the leaving group Y in compounds of formula II is especially hydroxy esterified by strong inorganic or organic acid. Examples of esterifying strong inorganic acids are mineral acids, for example hydrohalic acid, such as hydrochloric, hydrobromic or hydroiodic acid, sulfuric acid, or halosulfuric acid, such as fluorosulfuric acid. Examples of esterifying strong organic acids are sulfonic acids, for example lower alkanesulfonic acid optionally substituted by halogen, for example methanesulfonic or trifluoromethanesulfonic acid, or an aromatic sulfonic acid, for example a benzenesulfonic acid optionally substituted by lower alkyl, halogen or nitro, for example benzenesulfonic acid, p-toluenesulfonic acid or p-nitrobenzenesulfonic acid.

The reaction conditions in process (a) are preferably so chosen that the reaction proceeds substantially as a second-order nucleophilic substitution. Useful solvents are polar solvents, for example water, alcohols, for example methanol, ethanol or isopropanol, or mixtures thereof, or preferably dipolar aprotic solvents, for example acetone, acetonitrile, nitromethane, dimethyl sulfoxide or dimethylformamide. Preferably a base is added to the reaction mixture, for example an organic amine, especially a tertiary amine, such as triethylamine, tributylamine or pyridine, or an inorganic base, for example sodium or calcium carbonate. The reaction is carried out in a temperature range between −10° C. and +50° C., preferably at around room temperature, optionally under an inert gas atmosphere, for example under nitrogen.

Process (b) is carried out under the usual reaction conditions of reductive amination. The aldehyde of formula III is combined with the amine in the presence of hydrogen and a suitable hydrogenation catalyst, for example Raney nickel or platinum, in an inert hydrogenation solvent, for example an alcohol such as ethanol or ethyl acetate, at room temperature or above, and optionally under increased hydrogen pressure. Alternatively, the mixture of the aldehyde of formula III and the appropriate amine is treated with lithium cyanoborohydride in aqueous or alcoholic solution, for example in methanol, at a pH between 4 and 7, or with sodium borohydride in aqueous or alcoholic solution, for example in a mixture of ethanol and acetate buffer. Formic acid may also be used as the reducing agent.

In process (c) the leaving group Y in alkylating agents $R^0Y$ has one of the meanings detailed above under process (a) and is, for example, halide, such as chloride, bromide or iodide, hydrogensulfate, fluorosulfate, lower alkanesulfonate, such as methanesulfonate or trifluoromethanesulfonate, or arenesulfonate, such as benzenesulfonate, p-toluenesulfonate, p-bromosulfonate or p-nitrobenzenesulfonate. $R^0Y$ may be a monovalent alkylating agent representing $R^1Y$ or $R^2Y$, or a bivalent alkylating of the formula $Y-R^1-R^2-Y$. If $R^0Y$ is a bivalent alkylating agent, the reaction with the amino function of the compound of the formula IV may be stepwise, with or without isolation of the intermediate monoalkylated product, or occurring essentially in one step. When using a bivalent alkylating agent care is taken to avoid or minimize dimer formation by appropriate dilution techniques and slow addition. The reaction conditions in process (c) are those mentioned above under process (a).

Suitable reducing agents for process (d) are aluminum hydrides, for example lithium aluminum hydride, or boranes, for example diborane. The reduction is carried out in etheric solvents, for example diethyl ether, tetrahydrofuran or dimethoxyethane, at temperatures between −10° C. and the boiling point of the solvent, for example around room temperature, optionally under an inert gas atmosphere, for example under nitrogen.

Reduction of a compound of formula VI in process (e) can be carried out in one step, but is preferably carried out in a multi-step procedure reducing the keto function to an alcohol group, converting it to a leaving group, then finally reducing it to the methylene stage in a further reducing step.

In the one-step procedure hydrogenation may be carried out in the presence of a hydrogenation catalyst, for example Raney nickel, platinum or palladium on carbon, preferably at increased hydrogen pressure, in a polar, inert solvent, for example water, ethanol, acetic acid or mixtures thereof, at temperatures between 0° C. and 100° C. Alternatively the compound of formula VI is treated with hydrazine and strong base, for example aqueous potassium or sodium hydroxide in mono- or di-ethylene glycol at 50° to 150° C., or potassium tert-butoxide in dimethyl sulfoxide at around room temperature. The keto function may also be removed by zinc or zinc amalgam in aqueous hydrochloric acid.

In the preferred multi-step procedure the ketone of formula VI may be reduced to an alcohol by, for example, a hydride reducing agent, such as an aluminum hydride, for example lithium aluminum hydride, or a borohydride, for example sodium borohydride or diborane. Lithium aluminum hydride and diborane are used in etheral solvents, for example diethyl ether or tetrahydrofuran, at temperatures between 0° C. and the boiling point of the solvent. Sodium borohydride is used in water, an alcohol, for example methanol or ethanol, or mixtures thereof, at temperatures around room temperature. Alternatively the reduction is performed with aluminum alkoxides, for example aluminum tri-isopropoxide in the presence of excess isopropanol, in an inert solvent, for example toluene.

For the conversion of the hydroxy group into a leaving group, any of the usual esterifying methods are used. Suitable esterifying agents are, for example, hydrohalic acid, such as hydrochloric or hydrobromic acid, phosphorus halides, such as phosphorus tribromide, trichloride or pentachloride, triphenylphosphine in the presence of a halogen source, for example bromine or carbon tetrachloride, thionyl chloride, or sulfonyl chlorides derived from the lower alkane- or arenesulfonic acids mentioned under process (a). The esterification is preferably carried out in the presence of a base, for example a tertiary amine such as triethylamine or pyridine, in an inert solvent, for example chloroform, methylene chloride, diethyl ether or the like, at temperatures between 0° C. and the boiling point of the solvent.

The leaving group is replaced by hydrogen by catalytic hydrogenation in the presence of a hydrogenation catalyst, for example nickel, platinum or palladium on carbon, or by an aluminum or boron hydride, for example lithium aluminum hydride or sodium borohydride, under the conditions specified above in connection with these reducing agents. Alternatively, a tin hydride, for example tributyltin hydride or triphenyltin hydride, in an inert solvent, for example toluene, may be used.

In starting compounds and intermediates which are converted to the compounds of the invention in a manner described herein, functional groups present, such as carbonyl (formyl or keto), carboxy, amino and hydroxy groups, are optionally protected by conventional protecting groups that are common in organic chemistry.

Protected carbonyl, carboxy, amino and hydroxy groups are those that can be converted under mild conditions into free carbonyl, carboxy, amino and hydroxy groups without the molecular framework being destroyed or other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected, the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, New York 1973, T. W. Greene, "Protective Groups in Organic Synthesis", Wiley, New York 1984, and also in "The Peptides", Vol. 3 (edited by E. Gross and J. Meienhofer), Academic Press, London, New York 1981, as well as in Houben-Weyl, "Methoden der Organischen Chemie", Vol. 15/1, Georg Thieme Verlag, Stuttgart, 1974.

For example, a carbonyl group may be protected in the form of an acetal, e.g. as the ethylene or propylene acetal, or in the form of a thioacetal, e.g. as the propylene dithioacetal.

A carboxy group may be protected in the form of an easily cleaved ester, e.g. the benzyl ester, the tert-butyl ester, and the like as commonly used.

A basic primary or secondary amine may be protected in the form of easily cleaved amides, e.g. as acyl derivatives such as the benzyloxycarbonyl (carbobenzoxy) or the tert-butoxycarbonyl derivatives, or any other easily removable N-protecting groups.

A hydroxy group may be protected in the form of esters, e.g. as acyl derivatives such as the lower alkanoyl, benzyloxycarbonyl or lower alkoxycarbonyl esters, or such hydroxy group may be protected in the form of ethers, e.g. as the 2-tetrahydropyranyl or benzyl ethers, or as the trimethylsilyl or dimethyl-tert-butylsilyl ethers.

In a resulting protected compound of formula I or intermediate, in which one or more of the functional groups are protected, the protected functional groups can be liberated, in a manner, known per se, for example by means of solvolysis, e.g. hydrolysis with acid, by means of reduction, e.g. hydrogenolysis, or by treatment with oxidizing agents or fluorides.

Salts of compounds of formula I are obtained in customary manner, for example by treatment with an equimolar amount or a slight excess of the corresponding salt-forming acid in an alcoholic or etheral solvent. Salts can be converted into the free compounds in customary manner, for example by treatment with a suitable basic agent. Salts can be transferred into other salts by stepwise preparing the free compound and then the other salt thereof as described above, by treating the salt with an excess of the corresponding salt-forming reagent and, if possible, crystallizing the desired salt from a suitable solvent, or by treating the salt with the corresponding ion exchange resin.

In view of the close relationship between the free compounds and the compounds in the form of their salts, whenever a compound is referred to in this context, a corresponding salt is also intended, provided such is possible or appropriate under the circumstances.

In case diastereomeric mixtures of the above compounds or intermediates are obtained, these can be separated into single isomers by methods in themselves known, e.g. by fractional distillation, crystallization and/or chromatography.

The basic racemic products of formula I or basic intermediates can be resolved into the optical antipodes, for example, by separation of diastereomeric salts thereof, e.g., by the fractional crystallization of d- or l-(tartrate, dibenzoyltartrate, mandelate or camphorsulfonate) salts. Advantageously, the preferred more active of the antipodes of the compounds of this invention is isolated.

The starting materials used are known, or if novel, can be prepared according to the methods used in the references cited or as illustrated by the examples herein.

In particular, starting materials of formula II may be prepared from the corresponding compounds wherein Y is hydroxy by any of the esterifying methods mentioned above under process (e). Such alcohols are in turn available from the corresponding carboxylic acids by reduction with lithium aluminum hydride in diethyl ether at ambient temperature. Starting aldehydes of formula III may be obtained from the same corresponding carboxylic acids via reduction of the methyl or ethyl ester with diisobutylaluminum hydride or of the acid chloride with hydrogen in the presence of palladium on barium sulfate, or else by oxidation of the corresponding alcohol with chromium trioxide pyridine complex or manganese dioxide. Starting materials of formula IV are obtained in a process similar to process (a) or (d) wherein one of the substituents at nitrogen is replaced by hydrogen. Carboxylic acid amides of formula V are obtained from the corresponding carboxylic acids by reaction with thionyl chloride and the corresponding amine. Starting compounds of formula VI are conveniently prepared by reaction of the X-substituted benzothiopyran-4-one with either a formaldehyde-amine complex in a Mannich-type reaction or with an aminoethyl halide or sulfonate in the presence of base.

All of the above reactions are otherwise carried out according to standard methods, in the presence or absence of diluents, preferably such as are inert to the reagents and are solvents thereof, of catalysts, and/or of condensing or neutralization agents, and in air or under inert atmosphere, at low temperatures, room temperature or elevated temperatures, and at atmospheric or superatmospheric pressure.

The invention also comprises any modification of the above processes, wherein a compound resulting as an intermediate at any stage thereof is used as starting material and the remaining steps are carried out, or the process is discontinued at any stage thereof, or in which the starting material is formed under the reaction conditions or is used in the form of its salt or reactive derivative. In said processes of the invention those starting materials are advantageously selected which yield the above-described preferred embodiments of the invention.

The invention also relates to novel intermediates and processes for their manufacture.

Depending on the choice of starting materials and methods, the new compounds may be in the form of one enantiomer, racemate, or mixtures thereof, provided such are possible.

The compounds of the invention, including their salts, may also be obtained in the form of their hydrates, or include other solvents used for the crystallization.

The present invention additionally relates to the use in mammals of the compounds of formula I and their pharmaceutically acceptable salts, or pharmaceutical compositions thereof, as inhibitors of serotonergic function, particularly as serotonin-2 blockers (antagonists of serotonin at serotonin-2 receptors), for the treatment of disorders responsive to serotonin-2 receptor blockade, namely of psychotropic disorders, such as anxiety, schizophrenia, depression or mania, of gastrointestinal disorders such as ulcers, and of cardiovascular disorders such as hypertension.

More specifically, the invention relates to a method of inhibiting the effect of serotonin at central serotonin-2 receptors, and advantageously to a method of treatment of psychotropic disorders in mammals, e.g. such responsive to serotonin-2 blockade, particularly anxiety or psychotic disorders, using an effective amount of a compound of the invention, e.g. of formula I, or of a pharmaceutically acceptable salt thereof as pharmacologically active substances, preferably in the form of pharmaceutical compositions.

The dosage of active compound administered is dependent on the species of warm-blooded animal (mammal), the body weight, age and individual condition, and on the form of administration.

A unit dosage for a mammal of about 50 to 70 kg may contain between about 1 and 50 mg of the active ingredient.

The present invention also relates to the use of the compounds of the invention for the preparation of pharmaceutical compositions, especially pharmaceutical compositions having serotonin receptor modulating activity, particularly serotonin-2 blocking activity.

The pharmaceutical compositions according to the invention are those suitable for enteral, such as oral or rectal, and parenteral administration to mammals, including man, for the treatment of central nervous system disorders, such as anxiety, schizophrenia, depression and mania, or for the treatment of gastrointestinal or cardiovascular disorders, comprising an effective amount of a pharmacologically active compound of formula I or a pharmaceutically acceptable salt thereof, alone or in combination with one or more pharmaceutically acceptable carriers.

The pharmacologically active compounds of the invention are useful in the manufacture of pharmaceutical compositions containing an effective amount thereof in conjunction or admixture with excipients suitable for either enteral, parenteral or topical application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethylene glycol; for tablets also (c) binders, e.g. magnesium aluminum silicate, starch paste, gelatin, tragacanth, methyl cellulose, sodium carboxymethylcellulose and/or polyvinylpyrrolidone; if desired, (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions. Suppositories or topical lotions are advantageously made from fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods, respectively, and contain about 0.1 to 75%, preferably about 1 to 50%, of the active ingredient.

Suitable formulations for transdermal application include an effective amount of a compound of formula I with carrier. Advantageous carriers include absorbable pharmaceutically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

The following examples are intended to illustrate the invention and are not to be construed as being limitations thereon. Temperatures throughout are given in degrees Centigrade and all parts wherever given are parts by weight. If not otherwise stated, evaporations are carried out under reduced pressure, preferably between about 3 mbar and 100 mbar. The structure of final products, intermediates and starting materials is ascertained e.g. by analytical methods, such as microanalysis and spectroscopic characteristics, e.g. mass spectroscopy, infrared spectroscopy or nuclear magnetic resonance spectroscopy.

EXAMPLE 1

1-[(6-Fluoro-3,4-dihydro-2H-1-benzothiopyran-3-yl)methyl]-4-piperidinyl p-fluorophenyl ketone To a suspension of 2.178 kg (10.5 mol) p-fluorophenyl 4-piperidinyl ketone hydrochloride (R. L. Duncan et al., J. Med. Chem. 13, 1 (1970)), 1.008 kg (9.96 mol) triethylamine and 25 l dimethylformamide is added a solution of 3.053 kg (9.9 mol) (6-fluoro-3,4-dihydro-2H-1-benzothiopyran-3-yl)methyl iodide in 9 l dimethylformamide with stirring at 23° C. over 45 min. The suspension is stirred for 3 days at ambient temperature. The reaction is filtered and the filtrate concentrated at 80° C./4 mbar. The resulting oil is poured into a mixture of 20 l water and 24 l ethyl acetate, cooled to 5° C. and basified to pH 10 with concentrated ammonium hydroxide. The organic layer is separated, the aqueous solution extracted further with ethyl acetate, and the combined organic solutions washed with water and brine, dried over sodium sulfate and activated carbon, filtered, and concentrated at 50° C./4 mbar. The residue is triturated with heptane, filtered, washed twice with heptane, dried in vacuo and dissolved in dichloromethane. The solution is filtered from the insolubles, stirred with 1.27 kg Kieselgel 60 for 30 min., then filtered and evaporated at 45° C./4 mbar to give the title compound as a solid, m.p. 121°-124° C.

The hydrochloride of the title compound is prepared in the following way: 2.24 kg (5.78 mol) of the title compound as the free base and 28 l ethanol are combined and heated to 70° C., and 0.515 l (6.15 mol) concentrated hydrochloric acid is added. The hydrochloride crystallizes on cooling to 12° C. overnight. The solids are filtered, washed with ethanol and diethyl ether, and dried in vacuo to give the hydrochloride of the title compound, m.p. 238°–240° C. (dec.). The melting point is raised to 240°–243° C. by recrystallization from water.

The starting material is prepared as follows:

a) alpha-(p-Fluorophenylthiomethyl)acrylic acid: To a solution of 3.293 kg (25.69 mol) p-fluorothiophenol in 19.3 l methanol is added a solution of 3.32 kg (86%, 51.79 mol) potassium hydroxide in 3.32 l water dropwise with stirring at 0° C., then a solution of 4.452 kg (26.98 mol) alpha-bromomethylacrylic acid in 4.3 l methanol at such a rate as to maintain the reaction temperature below 15° C. The mixture is stirred for an additional 2 hours at 10° C., then poured into cold water (80 l) and acidified to pH 1 with concentrated hydrochloric acid. The product is filtered, washed with water and dried in vacuo, m.p. 110°–112° C.

b) 6-Fluoro-3,4-dihydro-2H-1-benzothiopyran-3-carboxylic acid: 1.105 kg (8.55 mol) N,N-diisopropylethylamine is added to a degassed mixture of 1.819 kg (8.56 mol) alpha-(p-fluorophenylthiomethyl)acrylic acid and 8.5 l o-dichlorobenzene with stirring at 30° C. under nitrogen. The resulting solution is heated to 165°–170° C. for 48 hours, then concentrated at 70° C./4 mbar. The residue is dissolved in diethyl ether and extracted into 2.5 N aqueous sodium hydroxide. The basic solution is acidified to pH 1 with concentrated hydrochloric acid. The solid is separated and dissolved in diethyl ether. The ether solution is washed with water and brine, dried over sodium sulfate, and evaporated in vacuo to give the title compound, m.p. 98°–102° C.

c) 6-Fluoro®-3,4-dihydro-2H-1-benzothiopyran-3-methanol: A solution of 2.13 kg (10.03 mol) 6-fluoro-3,4-dihydro-2H-1-benzothiopyran-3-carboxylic acid in 9.2 l tetrahydrofuran is added over 3 h to 11.568 mol borane in 22.5 l tetrahydrofuran, keeping the reaction temperature below 15° C. The mixture is stirred overnight at room temperature, then hydrolyzed with 1 l 50% aqueous acetic acid and concentrated at 50° C./4 mbar. The residue is diluted with 6 l water and basified with concentrated ammonium hydroxide to pH 10. The product is extracted into diethyl ether, and the ether solution is washed with brine, dried over sodium sulfate and evaporated to give the title compound as an oil.

d) (6-Fluoro-3,4-dihydro-2H-1-benzothiopyran-3-yl)methyl methanesulfonate: A solution of 2.687 kg (23.45 mol) methanesulfonyl chloride in 3.3 l dichloromethane is added over 2 hours to a solution of 4.215 kg (21.26 mol) 6-fluoro-3,4-dihydro-2H-1-benzothiopyran-3-methanol and 2.374 kg (23.46 mol) triethylamine in 34 l dichloromethane, keeping the reaction temperature below 15° C. The mixture is stirred overnight at room temperature, then hydrolyzed with 26 l water while cooling. The dichloromethane solution is separated, washed with water and brine, dried over sodium sulfate and evaporated. The oily residue is dissolved in 6 l ethyl acetate, filtered and treated with 6 l heptane. The title compound crystallizes out. It is filtered off, washed with ethyl acetate/heptane 1:3 and dried, m.p. 70.5°–72.5° C. Trituration with anhydrous ethyl ether raises the melting point to 72°–74° C.

e) (6-Fluoro-3,4-dihydro-2H-1-benzothiopyran-3-yl)methyl iodide: 5.53 kg (36.89 mol) sodium iodide is added to a solution of 3.361 kg (12.16 mol) (6-fluoro-3,4-dihydro-2H-1-benzothiopyran-3-yl)methyl methanesulfonate in 38.6 l acetone with stirring at 15° C. A gentle exothermic reaction occurs. The suspension is heated to reflux under a nitrogen atmosphere for 6 hours, then stirred at ambient temperature overnight and concentrated at 55° C./4 mbar. The solid is suspended in 22 l water and extracted with 4×10 l diethyl ether. The combined ether solutions are washed with brine, dried over sodium sulfate and activated carbon G-60, and evaporated in vacuo to give the title compound as an oil.

EXAMPLE 2

The following compounds are prepared using the method of example 1:

a) 6-Bromo-3-dimethylaminomethyl-3,4-dihydro-2H-1-benzothiopyran hydrochloride, m.p. 210°–222° C., from (6-bromo-3,4-dihydro-2H-1-benzothiopyran-3-yl)methyl iodide, m.p. 69°–71° C., and dimethylamine. The iodide in turn is prepared from the corresponding 6-bromo-3,4-dihydro-2H-1-benzothiopyran-3-carboxylic acid, m.p. 197°–203° C., by reduction to the alcohol, mesylation and treatment with sodium iodide.

b) 6-Bromo-3-piperidinomethyl-3,4-dihydro-2H-1-benzothiopyran hydrochloride, m.p. 212°–215° C.

c) Ethyl 1-[(6-fluoro-3,4-dihydro-2H-1-benzothiopyran-3-yl)methyl]piperidine-4-carboxylate, m.p. 64°–68° C.

EXAMPLE 3

3-Dimethylaminomethyl-3,4-dihydro-2H-1-benzothiopyran

To a suspension of 2 g lithium aluminum hydride in 100 ml ether is added 2 g of N,N-dimethyl-3,4-dihydro-2H-1-benzothiopyran-3-carboxamide dissolved in 50 ml ether in a dropwise fashion. The mixture is refluxed for 3 hours and the excess reagent decomposed by the slow dropwise addition of water with cooling. After filtration and concentration in vacuo the reaction mixture is acidified with ethanolic HCl to afford the hydrochloride of the title compound, m.p. 183°–187° C.

The starting material is prepared as follows:

N,N-Dimethyl-3,4-dihydro-2H-1-benzothiopyran-3-carboxamide

A mixture of 5.0 g of 3,4-dihydro-2H-1-benzothiopyran-3-carboxylic acid and 20 ml of thionyl chloride is heated at 90° C. for 30 minutes. The excess reagent is removed in vacuo and the residue dissolved in 100 ml methylene chloride and slowly treated with 5 ml dimethylamine dissolved in 10 ml methylene chloride. After 10 minutes at room temperatue the reaction mixture is washed with water, dried over magnesium sulfate and the solvent removed in vacuo to afford the title compound as an oil.

EXAMPLE 4

The following compounds are prepared using the method of example 3:

a) 3-Dimethylaminomethyl-6-methoxy-3,4-dihydro-2H-1-benzothiopyran hydrochloride, m.p. 184°–188° C., from 6-methoxy-3,4-dihydro-2H-1-benzothiopyran-3-carboxylic acid, m.p. 150°–154° C.

b) 3-Dimethylaminomethyl-6-fluoro-3,4-dihydro-2H-1-benzothiopyran hydrochloride, m.p. 185°–196° C., from 6-fluoro--3,4-dihydro-2H-1-benzothiopyran-3-carboxylic acid, example 1b.

c) 3-Dimethylaminomethyl-8-methoxy-3,4-dihydro-2H-1-benzothiopyran hydrochloride, m.p. 221°–223° C., from 8-methoxy-3,4-dihydro-2H-1-benzothiopyran-3-carboxylic acid, m.p. 140°–144° C.

d) 3-Dimethylaminomethyl-8-fluoro-3,4-dihydro-2H-1-benzothiopyran hydrochloride, m.p. 214°–219° C., from 8-fluoro-3,4-dihydro-2H-1-benzothiopyran-3-carboxylic acid, m.p. 147°–149° C.

e) 3-Diethylaminomethyl-6-fluoro-3,4-dihydro-2H-1-benzothiopyran hydrochloride, m.p. 146°–149° C.

f) 6-Fluoro-3-pyrrolidinomethyl-3,4-dihydro-2H-1-benzothiopyran hydrochloride, m.p. 162°–176° C.

g) 6-Fluoro-3-piperidinomethyl-3,4-dihydro-2H-1-benzothiopyran hydrochloride, m.p. 195°–199° C.

EXAMPLE 5

6-Fluoro-3-(2-piperidinoethyl)-3,4-dihydro-2H-1-benzothiopyran

The hydrochloride of the title compound, m.p. 160°–162° C., is prepared by lithium aluminum hydride reduction of the corresponding carboxylic acid amide following the procedure of example 3. The amide is prepared from the carboxylic acid using thionyl chloride and piperidine.

The starting material is prepared as follows: 6-Fluoro-3,4-dihydro-2H-1-benzothiopyran-3-ylacetic acid: A mixture of 3.8 g 6-fluoro-3-iodomethyl-3,4-dihydro-2H-1-benzothiopyran and 30 ml 0.5 M lithium cyanide in dimethylformamide is stirred at room temperature for 24 hours after which it is poured onto water. The product is extracted with ether. After drying over magnesium sulfate the solvent is removed in vacuo. This residue is refluxed in a mixture of 20 ml acetic acid and 20 ml 12 N HCl for 6 hours. The solvent is removed in vacuo, the residue is dissolved in 1 N NaOH and washed with ether. The aqueous phase is acidified with 3 N HCl and the product is extracted with ether. After drying over magnesium sulfate, the solvent is removed in vacuo. The residue is triturated with ether/hexane and affords the title compound, m.p. 125°–135° C.

EXAMPLE 6

3-(N-[(6-Fluoro-3,4-dihydro-2H-1-benzothiopyran-3-yl)methyl]-N-methylamino)propyl p-fluorophenyl ketone A mixture of 400 mg 6-fluoro-3-methylaminomethyl-3,4-dihydro-2H-1-benzothiopyran, 600 mg gamma-chloro-p-fluorobutyrophenone, 450 mg sodium iodide and 500 mg sodium bicarbonate in 15 ml dimethylformamide is heated with stirring at 100° C. for 40 minutes. The reaction mixture is poured onto water and the product is extracted with ether. After drying over magnesium sulfate the solvent is removed in vacuo and the residue subjected to flash chromatography on silica gel with ether/methylene chloride as the eluent. The major fraction is treated with ethanolic HCl and ether to afford the hydrochloride of the title compound, m.p. 140°–144° C.

The starting material 6-fluoro-3-methylaminomethyl-3,4-dihydro-2H-1-benzothiopyran is prepared from the corresponding iodide and methylamine according to example 1 and is used without further purification.

EXAMPLE 7

6-Fluoro-3-(4-[hydroxymethyl]piperidinomethyl)-3,4-dihydro-2H-1-benzothiopyran

A solution of 3.0 g ethyl 1-[(6-fluoro-3,4-dihydro-2H-1-benzothiopyran-3-yl)methyl]piperidine-4-carboxylate in 30 ml ether is added to a mixture of 2.5 g lithium aluminum hydride in 120 ml ether in a dropwise fashion with stirring and cooling. After 30 minutes at room temperature the excess reagent is decomposed with water, the reaction mixture is filtered and the solvent is removed in vacuo. The residue is treated with ethanolic HCl and ether and affords the hydrochloride of the title compound, m.p. 132°–136° C.

EXAMPLE 8

6-Fluoro-3-[4-(p-fluorobenzyloxymethyl)piperidinomethyl]-3,4-dihydro-2H-1-benzothiopyran To a solution of 600 mg 6-fluoro-3-(4-[hydroxymethyl]-piperidinomethyl)-3,4-dihydro-2H-1-benzothiopyran in 20 ml dimethyl sulfoxide is added 300 mg sodium hydride followed by 0.5 ml p-fluorobenzyl chloride. The reaction mixture is stirred for 6 hours. The reaction is diluted with water and the product is extracted with ether. After drying over magnesium sulfate the solvent is removed in vacuo and the residue subjected to flash chromatography on silica gel with ether/methylene chloride as the eluent. The compound is treated with ethanolic HCl and ether and affords the hydrochloride of the title compound, m.p. 176°–180° C.

EXAMPLE 9

(1-[(6-Fluoro-3,4-dihydro-2H-1-benzothiopyran-3-yl)methyl]-4-piperidinyl)methyl p-fluorobenzoate To a solution of 400 mg 6-fluoro-3-(4-[hydroxymethyl]-piperidinomethyl)-3,4-dihydro-2H-1-benzothiopyran and 200 mg triethylamine in 10 ml methylene chloride is added 221 mg p-fluorobenzoyl chloride. After 30 minutes at room temperature the reaction mixture is washed with 1 N sodium hydroxide, dried over magnesium sulfate and the solvent is removed in vacuo. The residue is triturated with ether/hexane to afford the title compound, m.p. 113°–114° C.

EXAMPLE 10

(1-[(6-Fluoro-3,4-dihydro-2H-1-benzothiopyran-3-yl)methyl]-4-piperidinyl)di(p-fluorophenyl)methanol To a solution of 1.75 g 4-bromofluorobenzene in 30 ml tetrahydrofuran (THF) at −78° C. is added 4 ml of 2.6 M n-butyl lithium in hexane at −78° C. After 15 minutes at −78° C. a solution of 3.37 g ethyl 1-[(6-fluoro-3,4-dihydro-2H-1-benzothiopyran-3-yl)methyl]-piperidine-4-carboxylate in 10 ml THF is added in a dropwise manner. The reaction mixture is allowed to warm to 0° C. over 30 minutes, then quenched with aqueous acetic acid. The products are extracted with ether. After drying over magnesium sulfate the solvent is removed in vacuo. Tertiary alcohol and ketone formed are separated by flash chromatography on silica gel with ether/hexane/triethylamine as the eluent. Fractions containing alcohol are combined and the oil treated with hot fumaric acid in ethanol to give the monofumarate of the title compound, m.p. 217°–220° C. The ketone fractions are triturated with ether/hexane to give the compound of example 1, 1-[(6-fluoro-3,4-dihydro-2H-1-benzothiopyran-3-yl)methyl]-4-piperidinyl p-fluorophenyl ketone, m.p. 123°–125° C.

EXAMPLE 11

Capsules 1,000 capsules, each containing 5 mg of the active ingredient, are prepared using the following formula:
1-[(6-Fluoro-3,4-dihydro-2H-1-benzothiopyran-3-yl)-methyl]-4-piperidinyl p-fluorophenyl ketone: 5.0 g
Lactose: 207.0 g Modified starch: 80.0 g
Magnesium stearate: 3.0 g All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 315 mg of said mixture each, using a capsule filling machine.

Analogously, capsules are prepared containing 2–50 mg of the other compounds disclosed and illustrated herein.

EXAMPLE 12

Tablets 10,000 tablets, each containing 10 mg of the active ingredient, are prepared using the following formula:

1-[(6-Fluoro-3,4-dihydro-2H-1-benzothiopyran-3-yl)methyl]-4-piperidinyl p-fluorophenyl ketone: 100 g
Lactose: 2535 g
Corn starch: 125 g
Polyethylene glycol 6000: 150 g
Talcum powder: 150 g
Magnesium stearate: 40 g
Purified water: q.s.

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35° C., broken on a screen with 1.2 mm openings and compressed into tablets, using concave punches uppers bisected.

Analogously, tablets are prepared containing 2–50 mg of one of the other compounds illustrated by the previous examples.

What is claimed is:

1. A compound of the formula

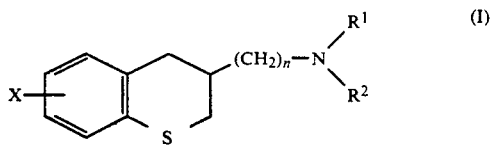

wherein n is one or two, X represents hydrogen, halogen, lower alkyl, hydroxy or lower alkoxy, $R^1$ is lower alkyl, $R^2$ is lower alkyl, substituted by A, or $R^1$ and $R^2$ together represent alkylene of 4 to 6 carbon atoms substituted by A, and A is hydroxymethyl, hydroxy-arylmethyl, hydroxy-diarylmethyl, lower alkoxymethyl, aryl-lower alkoxymethyl, lower alkanoyloxymethyl, aryl-lower alkanoyloxymethyl, aroyloxymethyl, lower alkanoyl, aryl-lower alkanoyl, aroyl, lower alkoxycarbonyl, or aryl-lower alkoxycarbonyl, or a salt thereof.

2. A compound according to claim 1 wherein n is one, X represents hydrogen, halogen, lower alkyl or lower alkoxy, $R^1$ is lower alkyl, $R^2$ is aroyl-lower alkyl, or $R^1$ and $R^2$ together represent straight, chain alkylene of 4 to 6 carbon atoms substituted by A, wherein A is hydroxymethyl, hydroxy-arylmethyl, hydroxy-diarylmethyl, lower alkoxymethyl, aryl-lower alkoxymethyl, lower alkanoyloxymethyl, aryl-lower alkanoyloxymethyl, aroyloxymethyl, lower alkanoyl, aryl-lower alkanoyl, aroyl, lower alkoxycarbonyl or aryl-lower alkoxycarbonyl; or an acid addition salt thereof.

3. A compound according to claim 1 of the formula

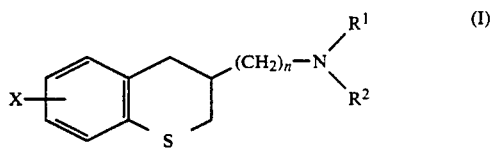

wherein n is one or two, X represents hydrogen, halogen, lower alkyl or lower alkoxy, $R^1$ is lower alkyl and $R^2$ is aroyl-lower alkyl or a pharmaceutically acceptable acid addition salt thereof.

4. A compound according to claim 3 wherein n is one, X represents hydrogen, halogen, lower alkyl or lower alkoxy, $R^1$ is lower alkyl and $R^2$ is aroyl-lower alkyl; or a pharmaceutically acceptable acid addition salt thereof.

5. A compound according to claim 3 wherein n is one, X represents fluoro and is located in the 6-position, and $R^1$ is lower alkyl and $R^2$ is p-fluorobenzoyl-lower alkyl, or a pharmaceutically acceptable acid addition salt thereof.

6. A compound according to claim 1 of formula

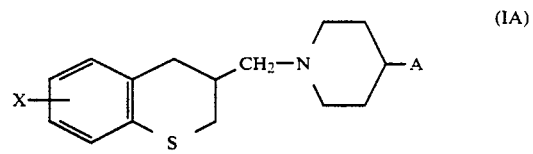

wherein X represents hydrogen, halogen, lower alkyl or lower alkoxy, and A is hydroxymethyl, alpha-hydroxybenzyl, alpha-hydroxydiphenylmethyl, lower alkoxymethyl, phenyl-lower alkoxymethyl, lower alkanoyloxymethyl, phenyl-lower alkanoyloxymethyl, benzoylmethyl, lower alkanoyl, phenyl-lower alkanoyl, benzoyl, lower alkoxycarbonyl or phenyl-lower alkoxycarbonyl, and wherein the phenyl group in phenyl, benzyl and benzoyl is unsubstituted or substituted by halogen in o-, m- or p-position; or a pharmaceutically acceptable acid addition salt thereof.

7. A compound according to claim 6 wherein X represents hydrogen, halogen, lower alkyl or lower alkoxy, and A is hydrogen, hydroxymethyl, alpha-hydroxydi(p-fluorophenyl)methyl, lower alkoxymethyl, p-fluorobenzyloxymethyl, p-fluorobenzoyloxymethyl, p-fluorobenzoyl, or lower alkoxycarbonyl; or a pharmaceutically acceptable acid addition salt thereof.

8. A compound according to claim 6 wherein X represents fluoro and is located in 6-position, and A represents alpha-hydroxydi(p-fluorophenyl)methyl, p-fluorobenzyloxymethyl, p-fluorobenzoyloxymethyl, or p-fluorobenzoyl; or a pharmaceutically acceptable acid addition salt thereof.

9. A compound according to claim 6 wherein X represents fluoro and is located in 6-position, and A represents p-fluorobenzoyl; or a pharmaceutically acceptable acid addition salt thereof.

10. A pharmaceutical preparation for the treatment of psychotropic, gastrointestinal and cardiovascular disorders responsive to serotonin-2 receptor antagonist activity comprising an effective amount of a compound of formula I as claimed in claim 1 or a pharmaceutically acceptable salt thereof together with a pharmaceutical carrier.

11. A pharmaceutical preparation for the treatment in mammals of psychotic disorders responsive to serotonin-2 receptor antagonist activity comprising an effective amount of a compound of claim 9 together with a pharmaceutical carrier.

12. A method of treating mammals suffering from anxiety, psychotic, gastrointestinal or cardiovascular disorders responsive to serotonin-2-receptor antagonist activity which comprises administering to a said mammal a therapeutically effective amount of a compound of formula I according to claim 1 or a pharmaceutically acceptable salt thereof.

13. A method of treating mammals suffering from psychotic disorders or anxiety responsive to serotonin-2-receptor antagonist activity which comprises administering to a said mammal in need thereof a therapeutically effective amount of a compound of claim 8.

14. A method of treating mammals suffering from psychotic disorders responsive to serotonin-2 receptor antagonist activity which comprises administering to a said mammal in need thereof a therapeutically effective antipsychotic amount of a compound of claim 9.

15. A method of treating mammals suffering from psychotic disorders or anxiety responsive to serotonin-2-receptor antagonist activity which comprises administering to a said mammal in need thereof a therapeutically effective amount of a compound of claim 3.

* * * * *